(12) United States Patent
Ziessel et al.

(10) Patent No.: US 9,388,202 B2
(45) Date of Patent: Jul. 12, 2016

(54) LUMINESCENT PROBES FOR BIOLOGICAL LABELING AND IMAGING, METHOD FOR PREPARING SAME

(71) Applicants: CENTRE NATIONAL DE LA RECHERCHE SCIENTIFIQUE, Paris (FR); UNIVERSITE DE STRASBOURG, Strasbourg (FR)

(72) Inventors: Raymond Ziessel, Souffelweyersheim (FR); Mathieu Starck, Strasbourg (FR); Alexandra Sutter, Wittelsheim (FR)

(73) Assignees: CENTRE NATIONAL DE LA RECHRCHE SCIENTIFIQUE, Paris (FR); UNIVERSITE DE STRASBOURG, Strasbourg (FR)

( * ) Notice: Subject to any disclaimer, the term of this patent is extended or adjusted under 35 U.S.C. 154(b) by 0 days.

(21) Appl. No.: 14/348,259

(22) PCT Filed: Oct. 11, 2012

(86) PCT No.: PCT/FR2012/052307
§ 371 (c)(1),
(2) Date: Mar. 28, 2014

(87) PCT Pub. No.: WO2013/054046
PCT Pub. Date: Apr. 18, 2013

(65) Prior Publication Data
US 2014/0228553 A1    Aug. 14, 2014

(30) Foreign Application Priority Data
Oct. 12, 2011  (FR) ...................................... 11 59222

(51) Int. Cl.
*C07F 9/58*    (2006.01)

(52) U.S. Cl.
CPC ...................................... *C07F 9/588* (2013.01)

(58) Field of Classification Search
CPC ...................................... C07F 5/00; C07F 9/58
See application file for complete search history.

(56) References Cited

FOREIGN PATENT DOCUMENTS

| EP | 0770610 | 5/1997 |
|----|---------|--------|
| FR | 2935973 | 3/2010 |
| WO | WO2007128873 | 11/2007 |

OTHER PUBLICATIONS

Harri Takalo et al. 50 Luminescenceof Europium (III) Chelates with 4-(Arylethynyl)pyridines as Ligands, Helvitica Chimica Acta, 76, 877-883, 1993.*
Ncchimi Nono Katia et al. Nonmacrocyclic Luminescent Lanthanide Complexes Stable in Biological Media, Inorg. Chem, 50, 1689-1697, 2011.*
Raymond Ziessel et al. Design and synthesis of phosphorylated pyridine-based ligands for lanthanide complexation. Part 1, Tetrahedron Letters, 53, 3713-3716, 2012.*
Search Report dated 2012.
"Luminescence of Europium (III) Chelates with 4-(Arylethynyl) pyridines as Ligands" Takalo et al. Dated Jan. 1, 1993.
"Formation of very stable and selective Cu(ii) complexes with a non-macrocyclic ligand: can basicity rival pre-organization?" Abada et al. Dated Jan. 1, 2010.

* cited by examiner

*Primary Examiner* — Michael G Hartley
*Assistant Examiner* — Jagadishwar Samala
(74) *Attorney, Agent, or Firm* — Sofer & Haroun, LLP

(57) ABSTRACT

The present invention relates to organic compounds that are usable as ligands for preparing complexes of lanthanides or of certain transition metals which are water-soluble, to a method for preparing same, and also to the use thereof as a fluorescent probe.

5 Claims, No Drawings

LUMINESCENT PROBES FOR BIOLOGICAL LABELING AND IMAGING, METHOD FOR PREPARING SAME

RELATED APPLICATIONS

This application is a National Phase Application of PCT/FR2012/052307, filed on Oct. 11, 2012, which in turn claims the benefit of priority from French Patent Application No. 11 59222 filed on Oct. 12, 2011, the entirety of which are incorporated herein by reference.

BACKGROUND

1. Field of the Invention

The present invention relates to organic compounds which may be used as ligands for the preparation of water-soluble complexes of lanthanides or of certain transition metals, to a process for preparing the same, and to the use thereof as fluorescent probes.

2. Description of Related Art

Lanthanide ion complexes have very particular spectroscopic properties that allow applications in the field of the detection by luminescence. These complexes have a very wide Stokes shift, very fine emission lines, of the order of a few nm, which are characteristic of the lanthanide ion used. They can emit in the visible or near infrared region, and have an extremely long lifetime of the excited state, which may be up to a millisecond. This last feature is an essential asset: it allows time-resolved detection (which makes it possible to eliminate the parasite fluorescence signals) and brings about a very large increase in the detection sensitivity of the complexes by luminescence microscopy or in fluoroimmunological analyses. Luminescent lanthanide ion complexes consequently have applications in the majority of the field of conventional fluorescence.

However, lanthanide ion complexes are generally difficult to obtain. Many properties of the complex are dependent on the structure of the ligand and of the lanthanide ion, especially the excitation efficacy of the complex, the degree of stability of the lanthanide complexation in competitive chemical medium and in serum medium (which must be high to prevent release of the cations), the quantum luminescence yield and the possibility of forming covalent bonds with the material to be labeled for the biological applications of the complexes. Adequate excitation of the complexes may be obtained when the ligand of the complex comprises heteroaromatic groups whose function is to capture light and transfer it to the lanthanide ion which will reemit. This phenomenon is known as the antenna effect. The choice of these heteroaromatic groups defines many spectroscopic properties of the final complex, especially the spectral excitation range and the quantum luminescence yield.

CN-1811429-A describes a complex of $Tb^{3+}$ and of a ligand which has a 2,6-dipyrazolylpyridine backbone in which each of the pyrazolyl groups bears a $-CH_2-N(CH_2CO_2H)_2$ group. Said complex is useful for detecting singlet oxygen. It is obtained via a process which consists in attaching the anthracene group to a dibromo-aminopyridine, and then in modifying the pyridyl group by reacting the bromine atoms with suitable reagents to replace each Br with a pyrazolyl group bearing a $-CH_2-N(CH_2CO_2H)_2$ group.

EP-0 770 610 describes lanthanide ion complexes in which the ligand is a 2,6-dipyrazolylpyridine backbone in which each of the pyrazolyl groups bears a $-CH_2-N(CH_2CO_2H)_2$ group. The preparation process consists in first preparing a dibromo 2,6-dipyrazolylpyridine compound, which is then modified to obtain the two $-CH_2-N(CHG_2CO_2H)_2$ end groups. This process does not make it possible to obtain compounds in which the pyridyl group bears substituents chosen to adjust the properties of the lanthanide complex in which said compounds constitute the ligand.

FR-2 935 973 describes ligands derived from 2,6-dipyrazolylpyridine in which each of the pyrazolyl groups bears a $-CH_2-N(CHG_2CO_2R)_2$ group in which each of the R groups represents H or an alkali metal or a quaternary ammonium group, the pyrazolyl groups also possibly bearing one or two substituents chosen from an alkyl group containing from 1 to 4 carbon atoms, or alternatively these two substituents together form a diradical forming an aromatic ring with the two carbon atoms that bear them. These ligands are capable of complexing lanthanide ions and find applications in labeling and biphotonic microscopy. However, they have poor solubility in water and great instability in purely aqueous medium, in saline medium or in purely biological medium.

OBJECTS AND SUMMARY

The aim of the present invention is to provide compounds that are useful as ligands for lanthanide or transition metal complexes which have improved solubility in water and in biological media, and also excellent chemical stability, very good luminescence properties and very long lifetimes.

This aim in achieved with the compounds that form the subject of the present invention and which will be described hereinbelow.

A compound according to the present invention corresponds to formula (I) below:

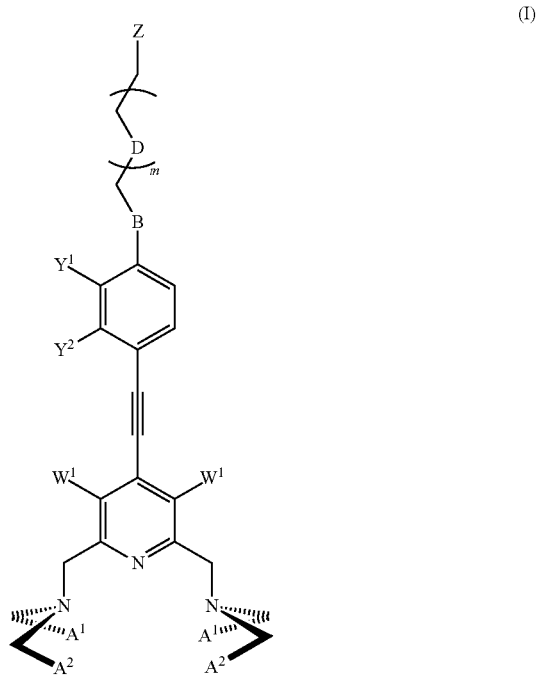

in which:
m is an integer ranging from 0 to 4;
$A^1$ represents a function $-COOR^1$ in which $R^1$ is a hydrogen atom or an alkali metal cation; or a group $A^2$;
$A^2$ represents a group $-P(O)(OCH_2CH_3)(OR^2)$ or $-P(O)(OR^2)_2$ in which $R^2$ represents a hydrogen atom or al alkali metal cation;

$W_1$ represents a hydrogen atom, a heteroatom, a halogen atom, a non-coordinating solubilizing function, a polyethylene glycol chain, or a function that is capable of changing the electron delocalization of the photon-collecting antenna;

each of the groups $Y^1$ and $Y^2$ represents an H atom, an amino or thiol group, or alternatively $Y^1$ and $Y^2$ together form a diradical forming one or more aromatic or heteroaromatic rings with the two carbon atoms that bear them;

B represents a bonding segment consisting of at least one group chosen from —CO—NH—, peptide groups containing from 1 to 4 amino acids, alkylene groups containing from 2 to 10 carbon atoms and optionally comprising at least one heteroatom in the carbon chain, and alkynyl groups containing from 2 to 10 carbon atoms and optionally comprising at least one heteroatom in the carbon chain;

D represents an oxygen or sulfur atom, a linear alkyl chain preferably containing from 1 to 4 carbon atoms, a cycloalkane which is preferably 2- to 3-membered or an aryl;

Z is:
$NH_2$, a halogen, a phosphate,
a group $COOR^3$ in which $R^3$ is H, an alkali metal cation, a quaternary ammonium group $N(R^4)_4^+$ in which $R^4$ is H or a linear alkyl chain preferably containing from 1 to 4 carbon atoms, a succinimide group —N—(CO—$CH_2$—$CH_2$—CO)— or a pentafluorophenyl group —$C_6F_5$;

a biotin function (—CO—$(CH_2)_4$—$C_5H_2N_2OS$), a polyheteroaromatic group or a crown ether, a silyl organic cluster or a mineral cluster;

a macroscopic support, for instance a silica bead, a nano-latex bead or any other support that can be functionalized, for instance mesoporous $TiO_2$, ZnO or NiO (A. Mishra et al. Angew. Chem. Int. Ed. 2009, 14, 2474).

According to the invention, the term "non-coordinating solubilizing function" means a function that is capable of solvating a molecule and of making it soluble in aqueous or serum medium such that the solubility of this molecule is of the order of a millimole per liter and which does not interact with lanthanide ions or transition metals. Among such non-coordinating solubilizing functions, mention may be made in particular of polyethylene glycol chains of various sizes, polysaccharides or complex carbohydrates, quaternary ammonium groups, etc.

According to the invention, the expression "function that is capable of changing the electron delocalization of the photon-collecting antenna" means any unsaturated function that is capable of giving rise to substantial electron delocalization. Among such functions, mention may be made in particular of aromatic rings, rings comprising heteroatoms, unsaturated bonds bearing an aryl or polyaryl group, or any unsaturated function.

According to the invention, the term "silyl organic cluster" means a cluster comprising silicon and oxygen without any metal atoms.

According to a preferred embodiment of the invention, $W^1$ represents a hydrogen atom.

Among the alkali metal cations mentioned for $R^1$ and $R^2$, mention may be made in particular of $K^+$, $Na^+$ and $Li^+$.

The compounds of formula (I) in which the groups $Y^1$ and $Y^2$ together represent a fused phenyl ring are particularly preferred.

A compound of formula (I) according to the present invention may be prepared from a compound corresponding to formula (II) below:

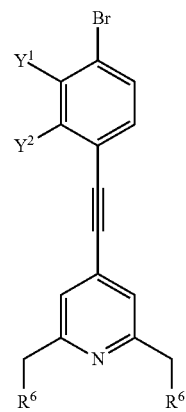

(II)

in which $R^6$ is chosen from the groups of formula $R^6$-a or $R^6$-b below:

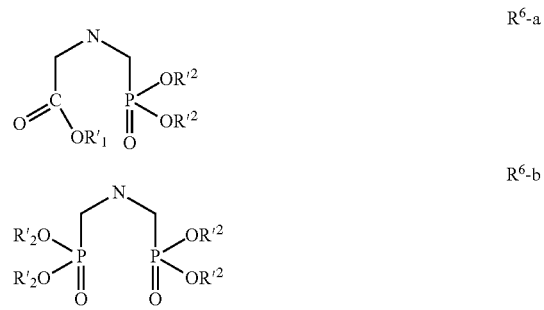

in which:
$R'^1$ represents a linear or branched $C_1$-$C_4$ alkyl radical, for instance an ethyl or tert-butyl radical;
$R'^2$ represents a $C_1$-$C_4$ radical, for instance an ethyl radical;
$Y^1$ and $Y^2$ are as defined for the compounds of formula (I) above.

The compounds of formula (III) in which the substituents $Y^1$ and $Y^2$ together form an aromatic ring, for instance a fused phenyl ring (referred to hereinbelow as compounds of formula (II')) may be prepared via a process comprising the following steps:

i) in a first step, 1,4-dibromonaphthalene (compound 1) is reacted with a source of acetylene, for instance propargyl alcohol to obtain a compound 2, ii) in a second step, compound 2 derived from step i) is deprotected in hot basic medium in the presence of a mineral base such as KOH or NaOH, to obtain a compound 3, iii) in a third step, coupling of compound 3 derived from step ii) is performed with a compound 4 of formula (III) below:

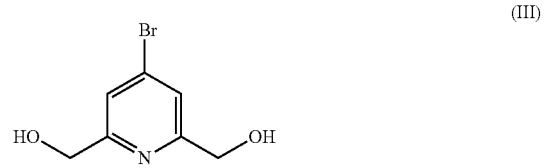 [SMILES: OCc1cc(Br)cc(CO)n1]

(III)

in the presence of a palladium catalyst, in an organic solvent under argon, and of a soluble organic base, to obtain a compound 5 of formula (IV) below:

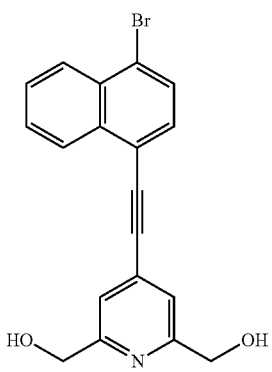

(IV)

iv) in a fourth step, the conversion of compound 5 into the dibromo compound 6 is performed in the presence of PBr$_3$ in chloroform medium using bromosuccinimide in the presence of triphenylphosphine:

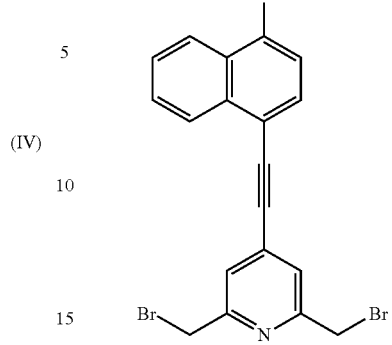

6 v) in a fifth step, substitution of the two bromine atoms on the pyridine ring of compound 7 is performed in an anhydrous solvent, for instance anhydrous acetonitrile, in the presence of a mineral base chosen, for example, from K$_2$CO$_3$, Na$_2$CO$_3$ and Cs$_2$CO$_3$ and of a compound chosen from the compounds of formula (V) below [NH(CH$_3$)COOR'$^1$)(CH$_2$P(O)(OR'$^2$)$_2$] and the compound of formula (VI) below [NH(CH$_2$(CH$_2$P(O)(OR'$^2$)$_2$)$_2$] in which R'$^1$ and R'$^2$, independently of each other, represent a linear or branched C$_1$-C$_4$ alkyl radical.

The process for preparing a compound of formula (II') may be represented by the reaction scheme 1 below, in which the radicals R'$^1$, R'$^2$, R$^5$ and R$^6$ have the meanings indicated above:

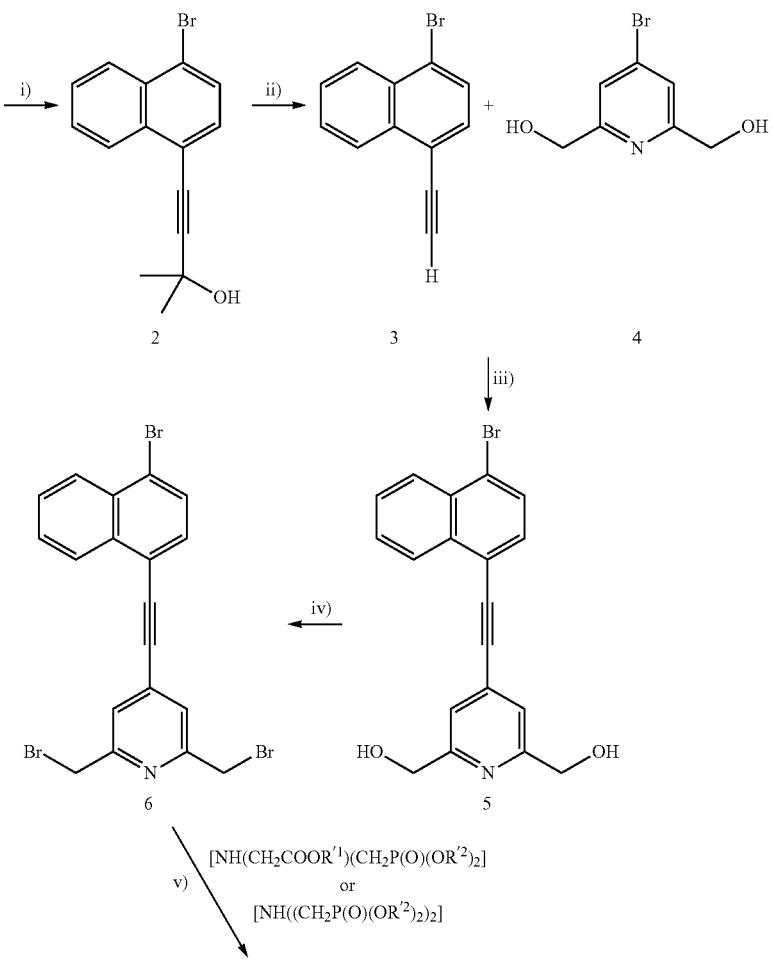

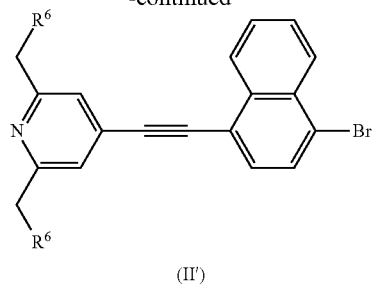

(II')

The compounds of formula (II) in which the radicals $Y^1$ and $Y^2$ together form an aromatic ring other than a phenyl group may be prepared via a process similar to that used above for the compounds of formula (II'), comprising steps i) to v) above, but using instead of 1,4-dibromonaphthalene in step i), a corresponding bromo compound, for example 2,3-dimethoxy-1,4-dibromobenzene.

A compound of formula (II) in which the substituents $Y^1$ and $Y^2$ are separate groups (referred to hereinbelow as the compound of formula (II")) may be prepared via a process similar to that described above for the compounds of formula (II'), comprising steps i) to v) above, but in which compound 1 is replaced in step i) with a 1,4-dibromophenyl compound bearing on the phenyl ring the desired substituents $Y^1$ and $Y^2$, i.e. a hydrogen atom or an amino or thiol group.

The process for preparing the compounds of formula (II') may be represented by the reaction scheme 2 below in which the radicals $R'^1$, $R'^2$, $R^5$ and $R^6$ have the meanings indicated above and $Y^1$ and $Y^2$ represent an H atom or an amino or thiol group:

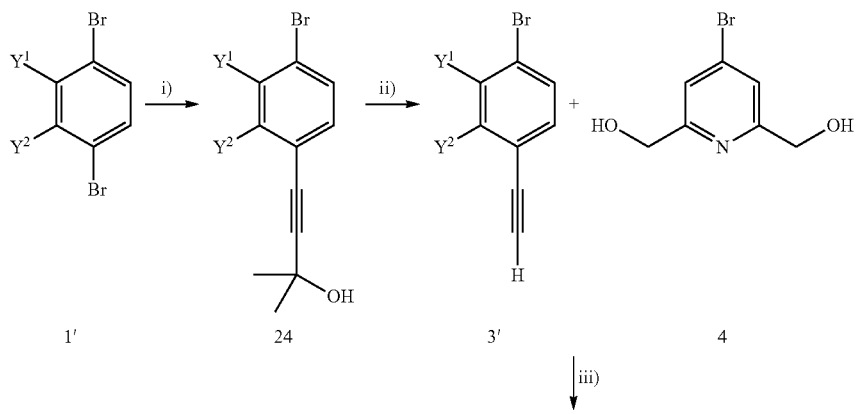

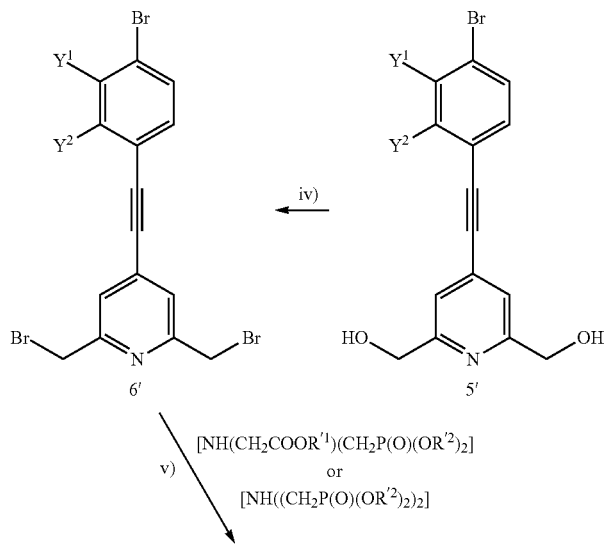

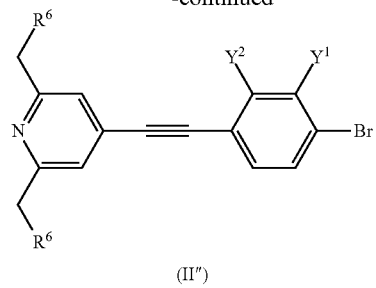

(II″)

More particularly, the process for preparing a compound of formula (I) according to the invention comprises:

- a first step in which the bromine of a compound of formula (II) is replaced with a group B—CH$_2$(D-CH$_2$)$_m$CH$_2$—Z in which D has the same meaning as that indicated above relating to the compounds of formula (I), by reaction with a suitable reagent, in the presence of an organometallic catalyst, in an organic solvent;
- a second step in which the groups R$^{t1}$ and R$^{t2}$ of the groups R$^6$-a or R$^6$-b are replaced, respectively, with groups R$^1$ and R$^2$, said groups being H or an alkali metal cation for R$^1$ or an alkali metal cation for R$^2$ as mentioned previously.

The replacement of the groups R$^{t1}$ and R$^{t2}$ of the linear alkyl type with a cation K$^+$, Na$^+$ or Li$^+$ may be performed with KOH, NaOH or LiOH, respectively, in a polar solvent (for example a CH$_3$OH/H$_2$O mixture) at a temperature of between 20 and 100° C., for example at 60° C., or alternatively using trimethylsilyl bromide in a solvent such as dichloromethane at room temperature followed by basic hydrolysis. The group COOK, COONa or COOLi may then, if necessary, be modified to an acid group by reaction with an acid such as HCl in water.

The replacement with H of groups R$^{t1}$ or R$^{t2}$ of the branched alkyl type may be performed by reaction with trifluoroacetic acid (TFA) in an aprotic organic solvent.

In the various steps of the process for preparing a compound of formula (II), the organic solvent may be THF, Et$_2$O, Et$_3$N, DMF, DMSO, toluene, CH$_2$Cl$_2$, or a mixture thereof (for example a THF/Et$_3$N mixture).

For the implementation of the first step of the process for preparing a compound of formula (I), the bromine atom of the compound of formula (II) may be subjected to various chemical reactions such as Stille, Heck, Sonogashira or Suzuki couplings, carboalkoxylation or carboamidation reactions.

The organometallic catalyst used in the first step is preferably a complex of Pd and triphenylphosphine, for example [Pd(PPh$_3$)$_2$Cl$_2$] or [Pd(PPh$_3$)$_4$]. The temperature is preferably between 20 and 120° C. The reagent used for reacting with the compound of formula (II) depends on the nature of the group B of the compound of formula (I). In the carboamidation (or, respectively, carboalkoxylation) reactions, B represents —CO—NH— (or, respectively, —CO—O—), the reagent used is an amine of formula Z—CH$_2$—(CH$_2$-D)$_m$-CH$_2$—NH$_2$ (or, respectively, an alcohol of formula Z—CH$_2$—(CH$_2$-D)$_m$-CH$_2$—OH), in which formulae Z, D and m have the meanings indicated above for the compounds of formula (I), in the presence of carbon monoxide. In the couplings of Sonogashira type, B represents —C≡C—, the reagent used comprises a true acetylenic group, H—C≡C—. According to a particular embodiment of the process for preparing the compounds of formula (I), and when the group B of the substituent B—CH$_2$(D-CH$_2$)$_m$CH$_2$—Z of the compound of formula (I) is a group —CO—NH—, then the first step is preferably performed under a stream of carbon monoxide in the presence of an aminoalkylate ester (such as an aminobutyrate ester, for instance ethyl aminobutyrate) at a preferential temperature of 70° C.

When the group B of the substituent B—CH$_2$(D-CH$_2$)$_m$CH$_2$—Z of the compound of formula (I) is a group —C≡C—, the first step of the process consists in reacting the compound of formula (II) with a corresponding reagent which bears an HC≡C— end group, for instance ethyl heptynoate. In this case, the reaction is preferably performed at a temperature of about 50° C. The organometallic catalyst is preferably a complex of palladium and triphenylphosphine, in particular Pd(PPh$_3$)$_2$Cl$_2$, in the presence of CuI or [Pd(PPh$_3$)$_4$].

A few examples of ligands, to which the invention is not, however, limited, are given below for purely illustrative purposes. Similar ligands may be obtained by replacing Na with one of the other groups R$^1$ or R$^2$ as defined previously.

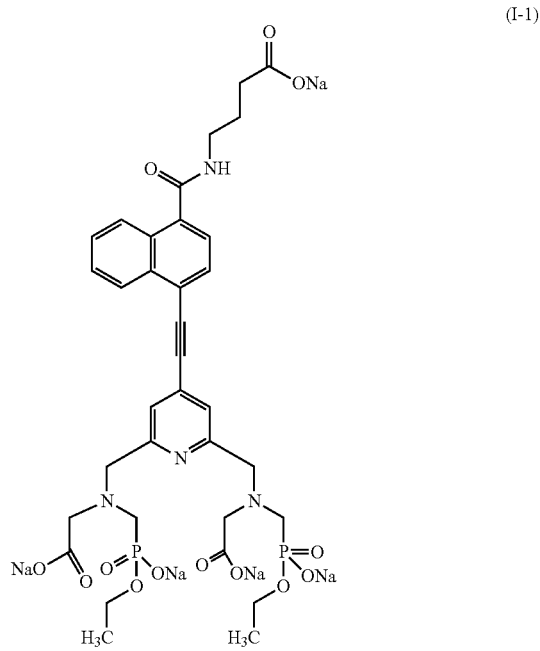

(I-1)

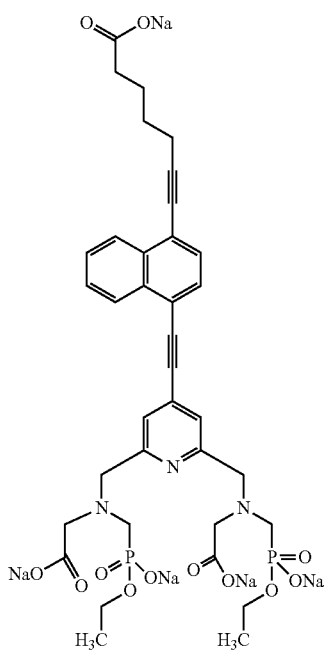

(I-2)

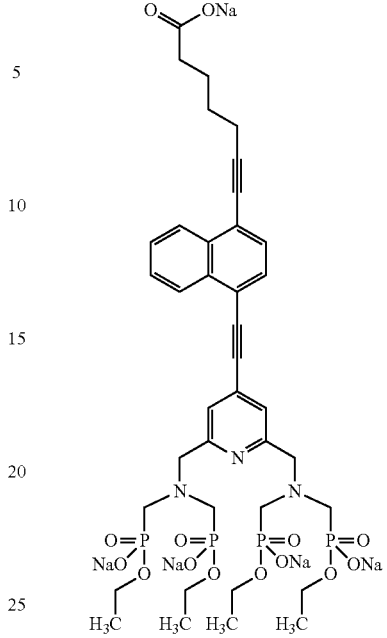

(I-4)

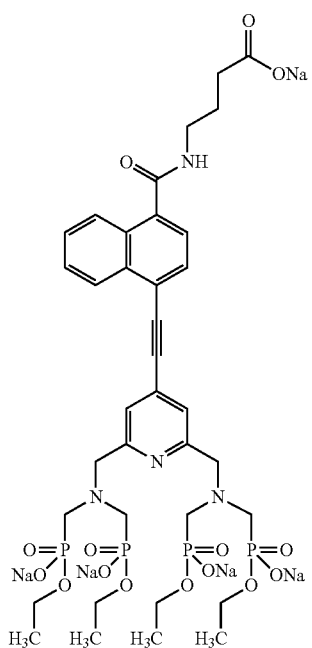

(I-3)

A complex of lanthanide or of a transition metal according to the invention comprises a lanthanide or transition metal ion complexed with a ligand of formula (I) as defined previously. The lanthanide ion is chosen from the ions $Gd^{3+}$, $Lu^{3+}$, $Eu^{3+}$, $Tb^{3+}$, $Dy^{3+}$, $Sm^{3+}$, $Er^{3+}$, $Yb^{3+}$, $Pr^+$ and $Nd^{3+}$. The transition metal ion may be chosen from the following metals Cu(II), Co(II), Mn(II or IV), Ni(II), Fe(III), Pd(II) and Pt(II).

A complex of lanthanide or of transition metal may be obtained by mixing equimolar amounts of a compound of formula (I) (preferably in sodium salt form) with a lanthanide salt or, respectively, a transition metal salt, heating of the mixture, cooling and neutralization to a pH of 6 to 8, followed by recovery of the complex at room temperature.

The lanthanide salt may be a nitrate, a chloride, a perchlorate or a triflate $Ln(CF_3SO_3)_3$.

The transition metal salt may be, for example, a chloride, acetate, or nitrate or any other compound that is soluble in water or alcohols.

In a particular embodiment, the compound of formula (I) and the lanthanide salt or the transition metal salt are mixed together in equimolar amounts in solution in water or in a MeOH/water mixture, the solution is heated for 2 to 3 hours at 60° C., cooled to room temperature and then neutralized, if necessary, to pH 7 by addition of NaOH, a quaternary ammonium hydroxide of HCl diluted in water. The complexes formed are then isolated by concentration of the mother liquors and precipitation from an $H_2O$/MeOH/THF/$Et_2O$ mixture.

The complexes according to the invention have varied applications, depending on the nature of the substituents on the pyridyl group of the ligand.

Their optical luminescence properties, the luminescence lifetimes and the brightness properties are exceptional, with quantum yields of about 38% for Tb, 18% for Eu and lifetimes of the excited states of greater than 3 milliseconds for the Tb(I-3) and Tb(I-4) complexes.

By way of example, all of the absorption and emission properties of the terbium and europium complexes synthesized from the ligands (I-1) to (I-4) in accordance with the invention are summarized in Table 1 below:

TABLE 1

| Nature of the complex | Absorption[a] | | Emission | | | |
|---|---|---|---|---|---|---|
| | $\lambda_{abs}$ (nm) | $\epsilon$ (M$^{-1}$·cm$^{-1}$) | $\tau$ (ms)[b] | | $\phi$ (%)[b] | |
| | | | H$_2$O | D$_2$O | H$_2$O | D$_2$O |
| Tb(I-1) | 268 | 6200 | 2.8 | 3.1 | 35 | 46 |
| | 348 | 48600 | | | | |
| Eu(I-1) | 266 | 5900 | 1.5 | 2.4 | 16 | 24 |
| | 349 | 48200 | | | | |
| Tb(I-2) | 270 | 6000 | 2.6 | 3.2 | 32 | 45 |
| | 349 | 48900 | | | | |
| Eu(I-2) | 265 | 5800 | 1.6 | 2.4 | 17 | 26 |
| | 347 | 48700 | | | | |
| Tb(I-3) | 272 | 6300 | 3.1 | 3.4 | 38 | 42 |
| | 353 | 50200 | | | | |
| Eu(I-3) | 270 | 6900 | 1.7 | 2.5 | 18 | 22 |
| | 352 | 50000 | | | | |
| Tb(I-4) | 272 | 6800 | 3.2 | 3.5 | 36 | 41 |
| | 352 | 50400 | | | | |
| Eu(I-4) | 268 | 6900 | 1.6 | 2.5 | 17 | 24 |
| | 350 | 50200 | | | | |

[a] in a 0.01 M TRIS/HCl buffer at pH = 7.0.
[b] Error estimated at ±15% on the quantum yield and ±5% on the lifetime $\tau$.

The parameters $\phi$ and $\tau$ represent, respectively, the quantum luminescence yields and the luminescence lifetimes. They may be measured in water and in D$_2$O.

In a preferred configuration of the invention, several stability tests show the absence of degradation of the fluorescent probe. It was demonstrated in particular that no loss of luminescence of the terbium and europium complexes was observed over several days when these complexes are dissolved in aqueous medium at neutral pH or in saline medium at concentrations of $10^{-5}$ to $10^{-6}$ M.

By way of example, the stability of the terbium complexes synthesized from the ligands (I-1) to (I-4) in accordance with the invention is given in Table 2 below. Various buffers in the presence of ligands capable of decomplexing the lanthanide ions were tested. For comparative purposes, Table 2 also gives the stability of a terbium complex TbL4 of the prior art corresponding to the following formula:

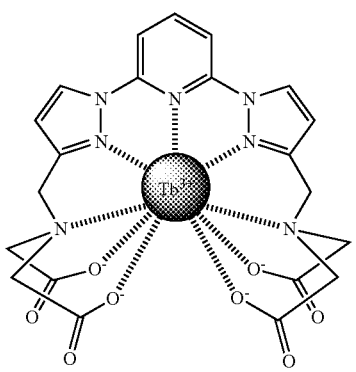

TbL4

TABLE 2

| | $\tau$ (ms) Estimated error ± 5% on $\tau$ | | | | |
|---|---|---|---|---|---|
| Buffers | TbL4 * | Tb(I-1) | Tb(I-2) | Tb(I-3) | Tb(I-4) |
| H$_2$O | 2.8 | 2.8 | 2.6 | 3.1 | 3.2 |
| Phosphate 0.1M, pH = 7.0 | 2.8 | 2.7 | 2.5 | 2.9 | 3.0 |
| Tris 0.1M, pH = 7.0 | 2.8 | 2.7 | 2.5 | 3.0 | 3.1 |
| Tris 0.1M - EDTA 10 mM, pH = 7.0 | 0.6 | 2.6 | 2.4 | 3.0 | 3.1 |
| Tris 50 mM - Serum 50%, pH = 7.0 | 0.2 | 2.6 | 2.4 | 3.0 | 3.0 |
| Tris 0.1M - KF 400 mM, pH = 7.0 | 0 | 2.6 | 2.5 | 2.9 | 3.0 |

* Complex not in accordance with the invention

This stability study shows that the complexes in accordance with the invention Tb(I-3) and Tb(I-4) have excellent stability with lifetimes of greater than 3 milliseconds in various aqueous media.

Moreover, the complexes in accordance with the invention have exceptional solubility in water. Their solubility is of the order of a millimole per liter.

Furthermore, the production and purification costs of these compounds make them very advantageous potential candidates for time-resolved biomedical and biological analysis for quantifying traces of analytes by specifically exciting the ligand which is considered as the photon-collecting antenna. The compounds in accordance with the invention make it possible to accommodate all of the lanthanides, and the absorption properties of the ligands are modulable as a function of the decoration provided by said ligand.

In particular, the complexes of the invention are useful for labeling compounds bearing an amine, alcohol, thiol, carboxylic acid or activated ester group. These compounds may be monomeric or polymeric molecules optionally in the form of beads. For this use, the group Z of the ligand of the complex is preferably a group —COOH, a group COONa, an activated ester of the N-hydroxysuccinimide ester or pentafluorophenol ester type, a Br, an I, or an amine.

When the ligand of the luminescent complex bears a recognition site electronically linked to the complexation structure of the ligand, the luminescence properties of the complex may be disrupted by the presence of an analyte which binds to the recognition site. By electronically coupling the recognition site to the central pyridine via acetylenic bonds, the interaction of the recognition site with its substrates induces electronic disruptions that are reflected by changes in luminescence of the lanthanide ion complexes.

Two-photon absorption microscopy and spectroscopy are relatively recent techniques and have the advantage, especially in microscopy, of allowing a significant improvement in spatial resolution by using low-energy photons. Virtually all of the luminescent markers studied in two-photon absorption are fluorescent organic compounds of Rhodamine® type. These organic compounds have very low Stokes shifts and broad emission bands (corresponding to a half-height width of greater than 50 nm). The luminescent lanthanide ion complexes according to the present invention have very high Stokes shifts and marrow emission bands. They consequently constitute compounds that are particularly advantageous for biphotonic microscopy and labeling, and very recent studies have demonstrated this possibility of Eu and Tb complexes,

[cf. in particular a) Law, G. L.; et al. *J. Am. Chem. Soc.* 2008, 130, 3714; b) Picot, A.; et al., *J. Am. Chem. Soc.* 2008, 130, 1532.]. The complexes of the invention in which the group B of the ligand of the complex is an amide function or a group C≡C, and the end group Z comprises an acid end function that can be transformed into an activated ester may be used as luminescent markers for two-photon absorption.

The complexes of the invention in which the end group Z of the ligand is a biotin group are useful for recognizing avidin, streptavidin and neuravidin.

DETAILED DESCRIPTION

The present invention is illustrated by the following examples, to which it is not, however, limited.

Example 1

Synthesis of the Compounds of Formulae (I-1) and (I-2)

1) First Step: Synthesis of Compound 2

To a degassed solution of 2.000 g of 1,4-dibromonaphthalene (compound 1 obtained from a commercial source) (6.99 mmol) in 60 ml of tetrahydrofuran (THF) containing 10 ml of diisopropylamine were added 0.588 g of propargyl alcohol (6.99 mmol), 0.490 g of $[Pd(PPh_3)_2Cl_2]$ (0.699 mmol) and then 0.133 g of CuI (0.699 mmol). The resulting solution was heated with stirring at 50° C. for 2 days. After aqueous work-up and extraction, the product was purified by column chromatography on flash silica using a gradient of petroleum ether in dichloromethane of from 50% to 0%. The expected compound 2 was obtained in the form of a white solid in a yield of 27%.

$^1$H NMR (300 MHz, CDCl$_3$) δ (ppm): 8.25 (m, 2H); 7.72 (d, $^3$J=7.7 Hz, 1H); 7.64 (m, 2H); 7.47 (d, $^3$J=7.7 Hz, 1H); 1.73 (s, 6H).

MS-ESI: 290.0 (98), 288.0 (100)

Elemental analysis for $C_{15}H_{13}BrO$:

|  | C | H |
|---|---|---|
| Calculated | 62.30 | 4.53 |
| Found | 62.11 | 4.25 |

2) Second Step: Synthesis of Compound 3

To a solution of 0.500 g of compound 2 (1.73 mmol) in 20 ml of a THF/H$_2$O mixture (15 ml/5 ml) was added an aqueous solution of KOH (0.484 g, 8.64 mmol) in 5 ml of water. After stirring for one hour, the compound was extracted with dichloromethane and the organic phase washed with saturated aqueous NH$_4$Cl solution. The compound was purified by chromatography on flash silica using a gradient of petroleum ether in dichloromethane of from 50% to 0%. The expected compound 3 was obtained in the form of a white solid in a yield of 95%.

$^1$H NMR (300 MHz, CDCl$_3$) δ (ppm): 8.27 (m, 2H); 7.77 (d, $^3$J=7.7 Hz, 1H); 7.71 (m, 2H); 7.50 (d, $^3$J=7.7 Hz, 1H); 3.24 (s, 1H).

MS-ESI: 232.0 (98), 230.0 (100)

Elemental analysis for $C_{12}H_7Br$:

|  | C | H |
|---|---|---|
| Calculated | 62.37 | 3.05 |
| Found | 62.21 | 2.89 |

3) Third Step: Synthesis of Compound 5

To a degassed solution of 0.329 g of compound 4 (1.51 mmol) prepared according to the process described by A. M. Raitsimring et al. (*J. Am. Chem. Soc.* 2007, 129, 14138) in a THF/triethylamine mixture (20 ml/7 ml) were added 0.349 g of compound 3 obtained above in step 2) (1.51 mmol) and 0.174 g of $[Pd(PPh_3)_4]$ (0.151 mmol). This solution was heated at 60° C. for 20 hours. The solvent was evaporated off on a rotavapor and the product extracted with dichloromethane. Purification was performed by flash chromatography on silica, using a gradient of methanol in dichloromethane of from 2% to 20%. The expected compound 5 was obtained in a yield of 67%.

$^1$H NMR (300 MHz, CDCl$_3$) δ (ppm): 8.36 (m, 2H); 7.71 (s, 2H); 7.66 (m, 2H); 7.43 (s, 2H); 4.84 (s, 4H); 1.68 (m, 2H).

MS-ESI: 369.0 (98), 367.0 (100)

Elemental analysis for $C_{19}H_{14}NO_2Br$:

|  | C | H | N |
|---|---|---|---|
| Calculated | 61.97 | 3.83 | 3.80 |
| Found | 61.69 | 3.64 | 3.51 |

4) Fourth Step: Synthesis of Compound 6

To a solution of 0.300 g of compound 5 obtained above in the preceding step (0.815 mmol) in 20 ml of chloroform was added 0.661 g of PBr$_3$ (2.44 mmol), and the solution was stirred at room temperature for 1 hour. 0.330 g of PBr$_3$ (1.22 mmol) was then added and the mixture was refluxed for 1 hour. The total conversion of compound 5 into compound 6 was monitored by thin-layer chromatography (TLC). After cooling, the reaction medium was poured cautiously into an aqueous NaCl solution at 0° C. The solvent was evaporated off on a rotavapor and the residue was extracted with dichloromethane. Purification was performed by flash chromatography on silica, using a gradient of petroleum ether in dichloromethane of from 70% to 50%. The expected compound 6 was obtained in a yield of 78%.

$^1$H NMR (300 MHz, CDCl$_3$) δ (ppm): 8.35 (m, 2H); 7.72 (s, 2H); 7.67 (m, 2H); 7.57 (s, 2H); 4.57 (s, 4H).

MS-ESI: 495.0 (98), 493.0 (100)

Elemental analysis for $C_{19}H_{12}NBr_3$:

|  | C | H | N |
|---|---|---|---|
| Calculated | 46.19 | 2.45 | 2.84 |
| Found | 45.83 | 2.24 | 2.63 |

5) Fifth Step: Synthesis of Compounds 7 and 8

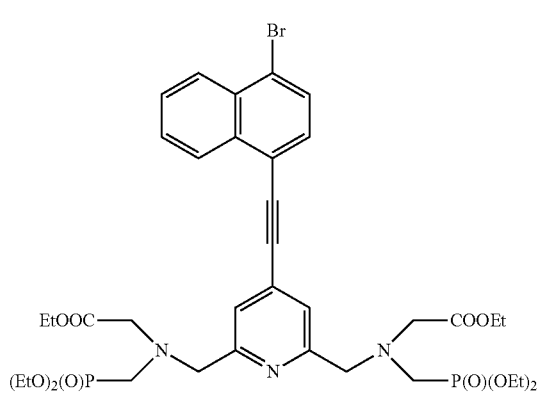

8

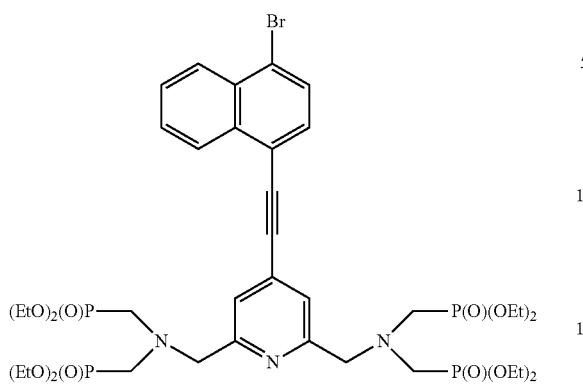

Synthesis of Compound 7

To a solution of 150.0 mg of compound 6 obtained above in the preceding step (0.304 mmol) in 20 ml of anhydrous acetonitrile were added 192.5 mg (0.760 mmol) of glyphosate derivative of formula NH[{CH$_2$PO(OEt)$_2$}(CH$_2$COOEt)] (prepared according to the reference S. Aime et al., Chem. Eur. J. 2006, 6, 2609-2617) and 209.8 mg of K$_2$CO$_3$ (1.520 mmol). The resulting solution was heated with stirring at 60° C. for 36 hours under argon. The product was purified by column chromatography on silica, using a mixture of solvents (from 0/10 to 2/8 (v/v) MeOH/CH$_2$Cl$_2$). The expected compound 7 was obtained in the form of a white solid in a yield of 70%.

$^1$H NMR (300 MHz, CDCl$_3$) δ (ppm): 8.38 (m, 2H); 7.74 (s, 2H); 7.69 (m, 2H); 7.60 (s, 2H); 4.20-4.09 (m, 12H); 4.00 (s, 4H); 3.60 (s, 4H); 3.16 (s, 4H); 1.34-1.16 (m, 18H).

$^{31}$P NMR {$^1$H} (CDCl$_3$, 161 MHz): δ 24.77.

MS-ESI: 839.2 (98), 837.2 (100).

Elemental analysis for C$_{37}$H$_{50}$N$_3$O$_{10}$P$_2$Br:

|  | C | H | N |
|---|---|---|---|
| Calculated | 52.99 | 6.01 | 5.01 |
| Found | 52.65 | 5.71 | 4.83 |

Synthesis of Compound 8

To a solution of 150.0 mg of compound 6 obtained above in the preceding step (0.304 mmol) in 20 ml of anhydrous acetonitrile were added 241.2 mg (0.760 mmol) of derivative aminobis(methylenediethyl phosphite) and 210 mg of anhydrous K$_2$CO$_3$ (1.520 mmol). The resulting suspension was heated at 60° C. for 12 hours under argon. The compound was purified by chromatography on silica gel, using a mixture of solvents (from 0/10 to 4/6 (v/v) MeOH/CH$_2$Cl$_2$) and gave the expected compound 8 in the form of a white solid in a yield of 72%.

$^1$H NMR (300 MHz, CDCl$_3$) δ (ppm): 8.32 (m, 2H); 7.69 (s, 2H); 7.65 (m, 2H); 7.59 (s, 2H); 4.11-4.07 (m, 16H); 4.02 (s, 4H), 3.16 (s, 4H); 3.12 (s, 4H); 1.25 (t, J=7.0 Hz, 24H).

$^{31}$P NMR {$^1$H} (CDCl$_3$, 161 MHz): δ 24.62.

MS-ESI 967.1 (98), 965.2 (100).

Elemental analysis for C$_{39}$H$_{60}$N$_3$O$_{12}$P$_4$Br:

|  | C | H | N |
|---|---|---|---|
| Calculated | 48.46 | 6.26 | 4.35 |
| Found | 48.24 | 5.87 | 4.11 |

6) Sixth Step: Synthesis of the Precursors of the Compounds I-1 and I-2, Two Examples of which are Compounds 9 and 10

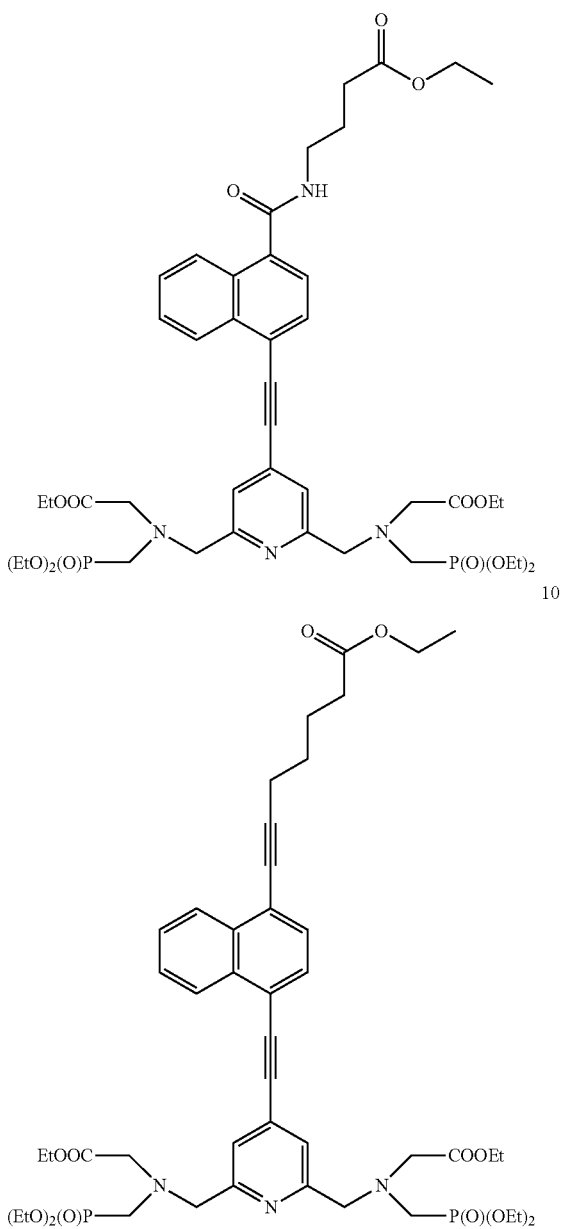

Synthesis of Compound 9

To a solution of 100.0 mg (0.119 mmol) of compound 7 obtained above in the preceding step, in a mixture of toluene (10 ml)/triethylamine (5 ml), were added 30.0 mg of 4-ethylaminobutyrate hydrochloride (0.179 mmol) and 8.3 mg of Pd(PPh$_3$Cl$_2$) (0.012 mmol). The resulting solution was heated at 70° C. for 12 hours under a continuous stream of CO at atmospheric pressure. The expected compound 9 was obtained in the form of a white solid after purification by chromatography on silica gel with a mixture of solvents as eluent (from 0/10 to 3/7 MeOH/CH$_2$Cl$_2$), in a yield of 64%.

$^1$H NMR (200 MHz, CDCl$_3$) δ (ppm): 8.34 (m, 2H); 7.77 (s, 2H); 7.66 (m, 2H); 7.58 (s, 2H); 4.22-4.00 (m, 14H); 4.06

(s, 4H); 3.66 (s, 4H); 3.27 (t, J=7.0 Hz, 2H); 3.16 (s, 4H); 2.31 (t, J=7.0 Hz, 2H); 1.96 (m, 2H); 1.37-1.15 (m, 21H).

$^{31}$P NMR {$^1$H} (CDCl$_3$, 161 MHz) δ 24.74

MS-ESI: 916.3 (100).

Elemental analysis for $C_{44}H_{62}N_4O_{13}P_2$:

|  | C | H | N |
|---|---|---|---|
| Calculated | 57.63 | 6.82 | 6.11 |
| Found | 57.45 | 6.49 | 5.88 |

Synthesis of Compound 10

To a degassed solution of 100.0 mg (0.119 mmol) of compound 7 as prepared above in the preceding step in a mixture of 6 ml of THF and 2 ml of triethylamine were successively added 7.7 mg of Pd(PPh$_3$Cl$_2$) (0.011 mmol), 2.1 mg of CuI (0.011 mmol) and 27.6 mg of ethyl hept-6-ynoate (0.179 mmol). The solution obtained was heated at 50° C. overnight. The product was purified by chromatography using a variable mixture of dichloromethane/methanol (from 0/10 to 3/7 v/v MeOH/CH$_2$Cl$_2$) and gave the expected compound 10 in the form of a white solid, in a chemical yield of 72%.

$^1$H NMR (300 MHz, CDCl$_3$) δ (ppm): 8.37 (m, 2H); 7.75 (s, 2H); 7.71 (m, 2H); 7.59 (s, 2H); 4.18-4.11 (m, 14H); 4.05 (s, 4H); 3.55 (s, 4H); 3.17 (s, 4H); 2.15 (m, 4H); 1.56 (m, 4), 1.32-1.11 (m, 21H).

$^{31}$P NMR {$^1$H} (CDCl$_3$, 161 MHz): δ 24.89.

MS-ESI 911.3 (100).

Elemental analysis for $C_{46}H_{63}N_3O_{12}P_2$

|  | C | H | N |
|---|---|---|---|
| Calculated | 60.58 | 6.96 | 4.61 |
| Found | 60.41 | 6.61 | 4.43 |

7) Seventh Step: Synthesis of Compounds I-1 and I-2

Synthesis of Compound I-1

To a solution of 0.050 g of compound 9 obtained above in the preceding step (0.055 mmol) in a mixture of THF (5 ml) and methanol (10 ml) was added 1 ml of an aqueous sodium hydroxide solution (11.3 mg, 0.284 mmol). The solution was stirred at room temperature overnight. Slow addition of diethyl ether brought about precipitation of the desired compound I-1. This white precipitate was centrifuged at 6000 rpm, and washed with ether. The resulting compound was recrystallized twice by diffusion of ether into a concentrated methanol solution. The expected compound of formula I-1 was obtained in a yield of 60%.

$^1$H NMR (200 MHz, CDCl$_3$) δ (ppm): 8.33 (m, 2H); 7.75 (s, 2H); 7.66 (m, 2H); 7.56 (s, 2H); 4.17 (q J=7.0 Hz, 4H); 4.06 (s, 4H); 3.66 (s, 4H); 3.27 (t, J=7.0 Hz, 2H); 3.16 (s, 4H); 2.31 (t, J=7.0 Hz, 2H); 1.96 (m, 2H); 1.18 (t, J=7.0 Hz, 6H).

$^{31}$P NMR {$^1$H} (CDCl$_3$, 161 MHz); δ 28.56

MS-ESI (water+1% trifluoromethanesulfonic acid): 777.2 (100), 389.1 (35, doubly charged)

Elemental analysis for $C_{34}H_{37}N_4O_{13}P_2Na_5+H_2O$

|  | C | H | N |
|---|---|---|---|
| Calculated | 45.14 | 4.35 | 6.19 |
| Found | 44.93 | 4.08 | 5.76 |

Synthesis of Compound I-2

To a solution of 0.050 g of compound 10 obtained above in the preceding step (0.055 mmol) in a mixture of tetrahydrofuran (4 ml) and methanol (8 ml) was added 1 ml of an aqueous sodium hydroxide solution (11.3 mg, 0.283 mmol). The solution was stirred at room temperature overnight. Slow addition of diethyl ether brought bout precipitation of the desired compound I-2. This white precipitate was centrifuged at 6000 rpm, and washed with ether. The resulting compound was recrystallized twice by diffusion of ether into a concentrated methanol solution. The expected compound I-2 was obtained in a yield of 64%.

$^1$H NMR (300 MHz, CDCl$_3$) δ (ppm): 8.34 (m, 2H); 7.73 (s, 2H); 7.68 (m, 2H); 7.57 (s, 2H); 4.14 (q, J=7.0 Hz, 4H); 4.07 (s, 4H); 3.57 (s, 4H); 3.19 (s, 4); 2.19 (m, 4H); 1.58 (m, 4H), 1.17 (m, 6H).

$^{31}$P NMR {$^1$H} (CDCl$_3$, 161 MHz): δ 28.73

MS-ESI (water+1% trifluoromethanesulfonic acid): 772.2 (100), 386.6 (20, doubly charged)

Elemental analysis for $C_{36}H_{38}N_3O_{12}P_2Na_5+H_2O$

|  | C | H | N |
|---|---|---|---|
| Calculated | 48.06 | 4.48 | 4.67 |
| Found | 47.81 | 4.23 | 4.43 |

Example 2

Synthesis of Compounds of Formulae I-3 and I-4

1) First Step: Synthesis of the Precursors of Compounds I-3 and I-4, Two Examples of which are Compounds 11 and 12

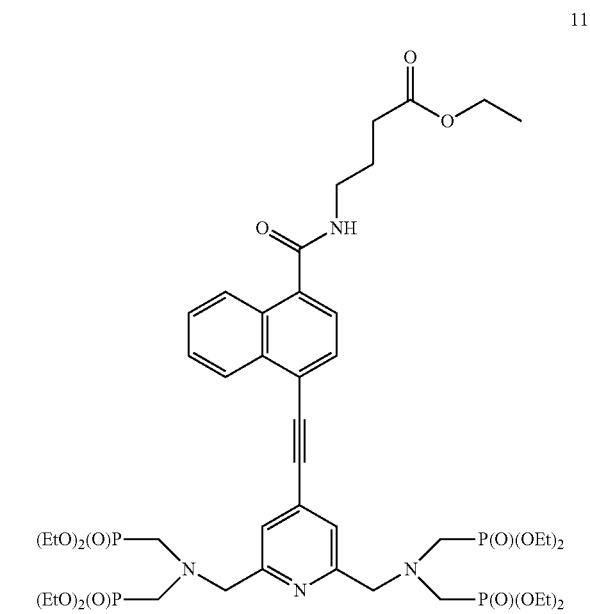

12

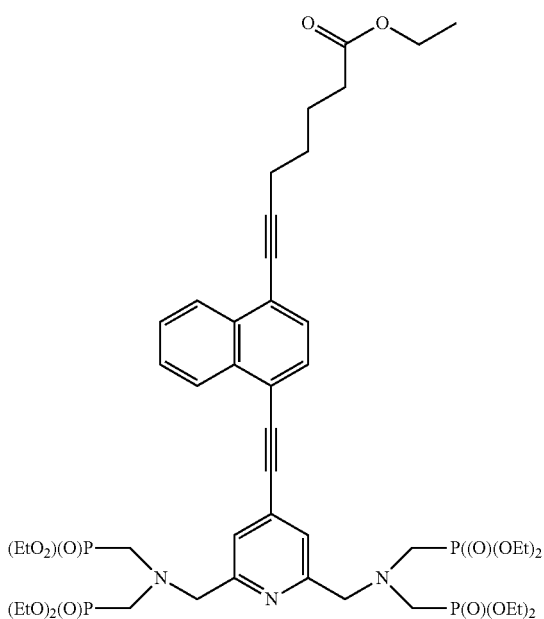

Synthesis of Compound 11

To a solution of 100.0 mg (1.103 mmol) of compound 8 obtained above in step 5 of Example 1, in a mixture of toluene (10 ml)/triethylamine (5 ml) were added 26.0 mg of 4-ethylaminobutyrate hydrochloride (0.155 mmol) and 7.2 mg of Pd(PPh$_3$Cl$_2$) (0.010 mmol). The resulting solution was heated at 70° C. for 12 hours under a continuous stream of CO at atmospheric pressure. The expected compound 11 was obtained in a yield of 74% in the form of a white solid after purification by chromatography on silica gel with a mixture of solvents as eluent (from 0/10 to 3/7 MeOH/CH$_2$Cl$_2$).

$^1$H NMR (200 MHz, CDCl$_3$) δ (ppm): 8.30 (m, 2H); 7.74 (s, 2H); 7.60 (m, 2H); 7.54 (s, 2H); 4.22-4.00 (m, 18H); 4.05 (s, 4H); 3.66 (s, 4H); 3.27 (t, J=7.0 Hz, 2H); 3.16 (s, 4H); 2.31 (t, J=7.0 Hz, 2H); 1.96 (m, 2H); 1.37-1.15 (m, 27H).

$^{31}$P NMR {$^1$H} (CDCl$_3$, 161 MHz) δ 27.56.

MS-ESI: 1045.0 (100).

Elemental analysis for C$_{46}$H$_{72}$N$_4$O$_{15}$P$_4$:

|  | C | H | N |
|---|---|---|---|
| Calculated | 52.87 | 6.94 | 5.36 |
| Found | 52.72 | 6.71 | 5.09 |

Synthesis of Compound 12

To a degassed solution of 100.0 mg (0.119 mmol) of compound 8 as prepared above in step 5) of Example 1, in a mixture of 6 ml of tetrahydrofuran and 2 ml of triethylamine, were successively added 7.7 mg of Pd(PPh$_3$Cl$_2$) (0.011 mmol), 2.1 mg of CuI (0.011 mmol) and 27.6 mg of ethyl hept-6-ynoate (0.179 mmol). The solution obtained was heated at 50° C. overnight. The product was purified by chromatography using a variable mixture of dichloromethane/methanol (from 0/10 to 3/7 v/v MeOH/CH$_2$Cl$_2$) and gave the expected compound 12 in the form of a white solid, in a chemical yield of 78%.

$^1$H NMR (300 MHz, CDCl$_3$) δ (ppm): 8.33 (m, 2H); 7.73 (s, 2H); 7.64 (m, 2H); 7.60 (s, 2H); 4.11-4.07 (m, 18H); 4.02 (s, 4H), 3.16 (s, 4H); 3.12 (s, 4H); 2.15 (m, 4H); 1.55 (m, 4), 1.25 (m, 27H).

$^{31}$P NMR {$^1$H} (CDCl$_3$, 161 MHz): δ 24.75.

MS-ESI 1039.3 (100).

Elemental analysis for C$_{48}$H$_{73}$N$_3$O$_{14}$P$_4$:

|  | C | H | N |
|---|---|---|---|
| Calculated | 55.43 | 7.07 | 4.04 |
| Found | 55.29 | 6.72 | 3.82 |

2) Second Step: Synthesis of Compounds I-3 and I-4

Synthesis of Compound I-3

To a solution of 0.060 g of compound 11 (0.057 mmol) as prepared above in the preceding step, in a mixture of tetrahydrofuran (5 ml) and methanol (10 ml), was added 1 ml of aqueous sodium hydroxide solution (11.9 mg, 0.298 mmol). The solution was stirred at room temperature overnight. Slow addition of diethyl ether brought about precipitation of the desired compound I-3. This white precipitate was centrifuged at 6000 rpm and washed with ether. The resulting compound was recrystallized twice by diffusion of ether into a concentrated methanol solution. The expected compound I-3 was obtained in a yield of 66%.

$^1$H NMR (200 MHz, CDCl$_3$) δ (ppm): 8.30 (m, 2H); 7.72 (s, 2H; 7.64 (m, 2H); 7.54 (s, 2H); 4.14 (q, J=7.0 Hz, 8H); 4.06 (s, 4H); 3.66 (s, 4H); 3.27 (t, J=7.0 Hz, 2H); 3.16 (s, 4H); 2.31 (t, J=7.0 Hz, 2H); 1.96 (m, 2H); 1.18 (t, J=7.0 Hz, 12H).

$^{31}$P NMR {$^1$H} (CDCl$_3$, 161 MHz): δ 28.54

MS-ESI (water+1% trifluoromethanesulfonic acid): 905.2 (100), 453.1 (25, doubly charged)

Elemental analysis for C$_{36}$H$_{47}$N$_4$O$_{15}$P$_4$Na$_5$+2H$_2$O

|  | C | H | N |
|---|---|---|---|
| Calculated | 41.15 | 4.89 | 5.33 |
| Found | 40.81 | 4.62 | 5.03 |

Synthesis of Compound I-4

To a solution of 0.060 g of compound 12 obtained above in the preceding step (0.058 mmol), in a mixture of tetrahydrofuran (4 ml) and methanol (8 ml), was added 1 ml of aqueous sodium hydroxide solution (12.0 mg, 0.300 mmol). The solution was stirred at room temperature overnight. Slow addition of diethyl ether brought about precipitation of the desired compound I-4. This white precipitate was centrifuged at 6000 rpm and washed with ether. The resulting compound was recrystallized twice by diffusion of ether into a concentrated methanol solution. The expected compound I-4 was obtained in a yield of 64%.

$^1$H NMR (300 MHz, CDCl$_3$) δ (ppm): 8.38 (m, 2H); 7.77 (s, 2H); 7.72 (m, 2H); 7.62 (s, 2H); 4.10 (q J=7.0 Hz, 8H); 4.04 (s, 4H); 3.64 (s, 4H); 3.21 (s, 4H); 2.21 (m, 4H); 1.62 (m, 4H), 1.21 (m, 12H).

$^{31}$P NMR {$^1$H} (CDCl$_3$, 161 MHz): δ 28.48

MS-ESI (water+1% trifluoromethanesulfonic acid): 900.2 (100), 450.5 (30, doubly charged).

Elemental analysis for C$_{38}$H$_{48}$N$_3$O$_{14}$P$_4$Na$_5$+2H$_2$O

|  | C | H | N |
|---|---|---|---|
| Calculated | 43.65 | 5.01 | 4.02 |
| Found | 43.43 | 4.76 | 3.87 |

The invention claimed is:
1. A compound of formula (I) below:

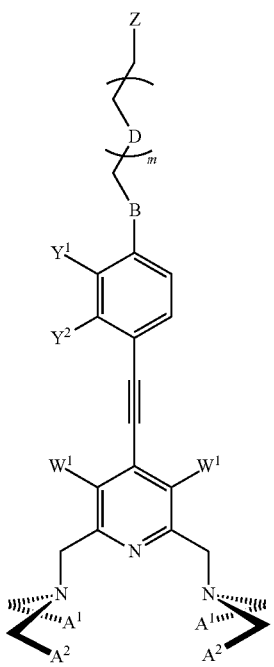

(I)

in which:
m is an integer ranging from 0 to 4;
A$^1$ represents a function —COOR$^1$ in which R$^1$ is a hydrogen atom or an alkali metal cation; or a group A$^2$;
A$^2$ represents a group —P(O)OCH$_2$CH$_3$)(OR$^2$) or —P(O)(OR$^2$) in which R$^2$ represents a hydrogen atom or an alkali metal cation;
W$_1$ represents a hydrogen atom, a heteroatom, a halogen atom, a non-coordinating solubilizing function, a polyethylene glycol chain, or a function that is capable of changing the electron delocalization of the photon-collecting antenna;
each of the groups Y$^1$ and Y$^2$ represents an H atom, an amino or thiol group, or alternatively Y$^1$ and Y$^2$ together form a diradical forming one or more aromatic or heteroaromatic rings with the two carbon atoms that bear them;
B represents a bonding segment consisting of at east one group chosen from —CO—NH— peptide groups containing from 1 to 4 amino acids, alkylene groups containing from 2 to 10 carbon atoms and optionally comprising at least one heteroatom in the carbon chain, and alkynyl groups containing from 2 to 10 carbon atoms and optionally comprising at least one heteroatom in the carbon chain;
D represents an oxygen or sulfur atom, a linear alkyl chain, a cycloalkane or an aryl;
Z is:
  NH$_2$, a halogen, a phosphate,
  a group COOR$^3$ in which R$^3$ is H, an alkali metal cation, a quaternary ammonium group N(R$^4$)$_4$$^+$ in which R$^4$ is H or a linear alkyl chain, a succinimide group —N—(CO—CH$_2$—CH$_2$—CO)— or a pentafluorophenyl group C$_6$F$_5$;
  a biotin function (—CO—(CH$_2$)$_4$—C$_5$H$_7$N$_2$OS); a polyheteroaromatic group or a crown ether,
  a silyl organic or mineral cluster;
  a macroscopic support.

2. The compound as claimed in claim 1, wherein W$^1$ represents a hydrogen atom.

3. The compound as claimed in claim 1 wherein R$^1$ and R$^2$ are chosen from K$^+$, Na$^+$ and Li$^+$.

4. The compound as claimed in claim 1, wherein the groups Y$^1$ and Y$^2$ together represent a fused phenyl ring.

5. The compound as claimed in claim 1, wherein said compound corresponds to one of the formulae (I-1) to (I-4) below:

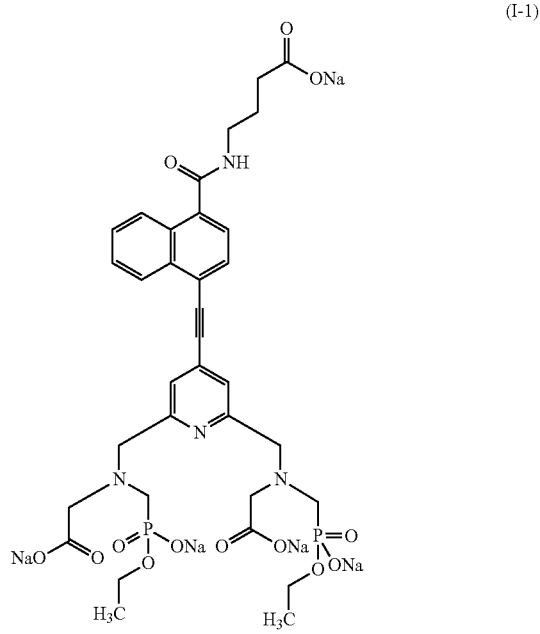

(I-1)

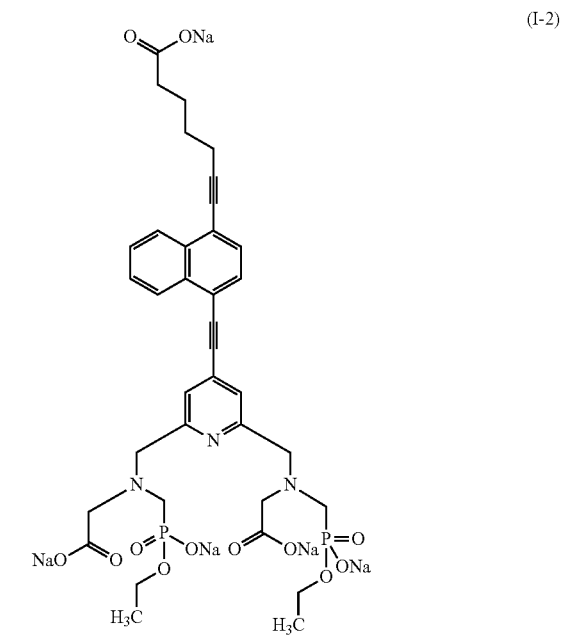

(I-2)

(I-3)
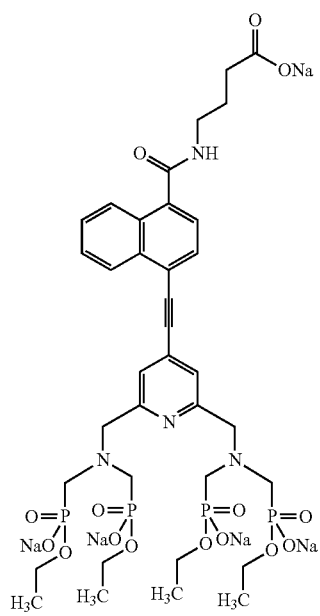
(I-4)
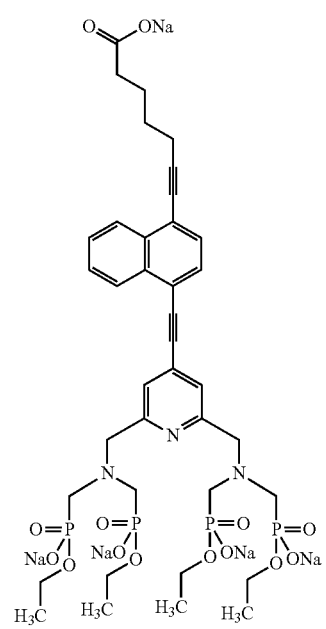
* * * * *